US005542426A

United States Patent [19]

Watanabe et al.

[11] Patent Number: 5,542,426

[45] Date of Patent: Aug. 6, 1996

[54] METHOD OF FABRICATING ULTRASONIC PROBE

[75] Inventors: Kazuhiro Watanabe; Yasushi Hara, both of Kawasaki, Japan

[73] Assignee: Fujitsu Limited, Kawasaki, Japan

[21] Appl. No.: 254,756

[22] Filed: Jun. 6, 1994

[30] Foreign Application Priority Data

Jun. 8, 1993 [JP] Japan .................................... 5-137681

[51] Int. Cl.[6] .............................. A61B 8/00; H04R 17/00

[52] U.S. Cl. ...................................... 128/662.03; 29/75.35

[58] Field of Search ......................... 128/662.03, 661.01; 29/25.35; 310/334, 357–358; 367/905, 155

[56] References Cited

U.S. PATENT DOCUMENTS

| | | | |
|---|---|---|---|
| 3,950,659 | 4/1976 | Dixon et al. | 310/8 |
| 4,460,841 | 7/1984 | Smith et al. | 310/334 |
| 4,518,889 | 5/1985 | Hoen | 310/357 |
| 5,396,143 | 3/1995 | Seyed-Bolorforosh et al. | 128/662.03 X |

*Primary Examiner*—Francis Jaworski
*Attorney, Agent, or Firm*—Staas & Halsey

[57] ABSTRACT

From a single material of unpolarized piezoelectric transducer, cut away are a piezoelectric transducer for fabrication of a probe and a piezoelectric transducer for observation of polarization states. Both the piezoelectric transducer for fabrication of a probe and the piezoelectric transducer for observation of polarization states are simultaneously subjected to the polarization processing (or depolarization processing) while observing polarization states of the piezoelectric transducer for observation of polarization states.

7 Claims, 14 Drawing Sheets

METHOD OF FABRICATING ULTRASONIC PROBE

BACKGROUND OF THE INVENTION

1. Field of the Invention

The present invention relates to a method of fabricating an ultrasonic probe in which inputted electric signals are converted into ultrasounds which are transmitted, while the received ultrasounds are converted into electric signals which are outputted.

2. Description of the Related Art

There has been generally used an ultrasonic diagnostic system for facilitating diagnoses of diseases of the viscera and the like, in which ultrasonic beams are transmitted inside of the human body and ultrasounds reflected by a tissue in the human body are received in the form of received signals, so that images in the human body involved in the received signals are displayed. In such an ultrasonic diagnostic system, there is used an ultrasonic probe which serves as a transducer wherein electric signals are converted into ultrasounds which are transmitted into the subject, while ultrasounds reflected by the inside of the subject are received and converted into electric signals.

FIG. 9 is a perspective view of an ultrasonic probe illustrated by way of example. FIG. 10 is a block diagram of circuits to be connected to the ultrasonic probe shown in FIG. 9.

The ultrasonic probe comprises a number of piezoelectric transducers 1 each made of for example piezo-electric ceramic (PZT ceramics) which are arranged in an array configuration in the horizontal direction (scan direction: x-direction). At the front side of an array of the piezoelectric transducers 1, there are formed common front electrodes **1*a* which are electrically connected with each other and earthed. And at the rear side of the array of the piezoelectric transducers 1, there are formed rear electrodes 1*b* which are independently of each other and are each connected to the associated lead wire 2. Further, at the front side of the array of the piezoelectric transducers 1, there are formed matching layers 3 each made of epoxy resin or the like and corresponding to the associated piezoelectric transducer 1, and in addition there is provided an acoustic lens 4 made of silicone rubber or the like for converging the ultrasounds transmitted from the ultrasonic probe with respect to the minor direction (y-direction) perpendicular to the scan direction (x-direction). And at the rear side of the array of the piezoelectric transducers 1, there is provided a backing 5 which is coupled through the rear electrode 1*b* to the array of the piezoelectric transducers 1**, for the purpose of reducing a duration of waves of ultrasounds and also of absorbing the ultrasounds radiated toward the rear side.

To transmit the ultrasonic acoustic waves within the subject (not illustrated) such as the human body by the use of the ultrasonic probe having the arrangement as mentioned above, pulse signals are applied from a transmission circuit 6 shown in FIG. 10 to the piezoelectric transducers 1, respectively, so that the respective piezoelectric transducers 1 radiate burst waves of the ultrasonic beams. The pulse signals, which are transmitted from the transmission circuit 6, are controlled in timing of transmission of the pulse signals in such a manner that the ultrasonic beams radiated from the respective piezoelectric transducers 1 are converged on a predetermined depth position inside of the subject.

Meanwhile, the ultrasounds radiated from the ultrasonic probe and reflected by the inside of the subject are received by the respective piezoelectric transducers 1 and be converted into received signals. The received signals are amplified suitably and then applied to a beamformer circuit 8 in which beamforming operation is conducted in such a way that the ultrasonic beams radiated from the respective piezoelectric transducers 1 are converged on a fixed or sequentially varied depth position inside of the subject.

The received signals undergone the beamforming operation in the beamformer circuit 8 are inputted to a signal processing circuit (not illustrated) in which image signals representative of images inside of the subject by the ultrasounds are generated on the basis of the received signals. The images may be displayed on, for example, a CRT display and the like, in accordance with the thus obtained image signals.

FIG. 11A is a view showing a sound pressure distribution of ultrasounds radiated from an array of piezoelectric transducers, FIG. 11B is a view showing a sound pressure profile of a section of an ultrasonic beam in case of the sound pressure distribution of radiation as shown in FIG. 11A, and FIG. 11C is a graphical representation showing the relations between the depth within the subject and the beam width of the minor axis direction, in case of the sound pressure distribution of radiation as shown in FIG. 11A.

As shown in FIG. 11A, when ultrasonic acoustic waves, which have even sound pressure of radiation throughout the center portion and the both edge portions of the piezoelectric transducers with respect to the minor axis direction, are sent out, there will be induced large side lobes on the ultrasonic beams within the subject, as shown in FIG. 11B. As a result, as shown in FIG. 11C, it is merely permitted that the ultrasonic beams are contracted only at the neighborhood of the focal point of the acoustic lens (refer to FIG. 9), and thus the beam diameter will be remarkably spread.

FIGS. 12A–12C are views similar to FIGS. 11A–11C, respectively, except that the sound pressure distribution of radiation is different with respect to the minor axis direction.

As shown in FIG. 12A, there is prepared an array of piezoelectric transducers each having a long board-like configuration and being arranged in the scan direction. The piezoelectric transducer is polarized in such a manner that intensity of the polarization is stepwise given with respect to the minor axis direction. To polarize the piezoelectric transducer in such a way that intensity of the polarization is stepwise given with respect to the minor axis direction, there is used, for example, the following technique.

FIG. 14 is a typical illustration showing a technique of polarizing the piezoelectric transducer in such a manner that intensity of the polarization is stepwise given with respect to the minor axis direction.

Generally, according to the polarization operation for the piezoelectric transducer, a hundreds volts/mm of electric field is applied for several minutes to several hours to good conductor electrodes disposed at two main planes (a front face and a rear face) of a transducer plate, which are placed over against each other, in the tens to hundreds °C. of temperature atmosphere. The polarization states can be controlled in accordance with these polarization conditions, that is, the polarization electric field, the polarization temperature and the polarization time. Setting up of a larger value of the polarization condition causes the polarization state of the piezoelectric transducer to be larger as a process proceeds from the unsaturation polarization to the saturation polarization.

For those reasons, as shown in FIG. 14, there are formed on one main plane (e.g. the rear face) of the piezoelectric transducer a plurality of good conductor electrodes each having a stripe-like configuration and extending in the longitudinal direction of the piezoelectric transducer, or the scan direction (a x-direction; refer to FIG. 9) when constructed as the ultrasonic probe, while a sheet of good conductor electrode is formed as a whole on another main plane (e.g. the front face) of the piezoelectric transducer. And between the respective stripe-like shaped electrodes at the rear face side and the opposite front side of electrode, as seen from the figure, applied are voltages which are larger as the location of the associated electrode is closer to the center of the piezoelectric transducer with respect to the minor axis direction, and in this condition the piezoelectric transducer is placed for a predetermined polarization time under a predetermined polarization temperature. Thus, there is built the piezoelectric transducer having a step-like shaped distribution of intensity of the polarization.

In this manner, when the piezoelectric transducer is polarized in such a way that a distribution of intensity of the polarization is stepwise given with respect to the minor axis direction, there will be obtained an electromechanical coupling factor having a distribution in compliance with such distribution of intensity of the polarization. Where the electromechanical coupling factor k is defined by the square root of the ratio of electric energy inputted to the piezoelectric transducer to mechanical energy with which the piezoelectric transducer vibrates when the electric energy is applied thereto, that is, as follows:

$$k=(\text{output mechanical energy}/\text{input electric energy})^{1/2} \quad (1)$$

The piezoelectric transducer undergone the polarization operation in the manner as mentioned above is segmented, as shown in FIG. 13B, into a number of pieces which are disposed on the ultrasonic probe to radiate ultrasounds. The radiated ultrasounds have each a sound pressure which is substantially in proportion to the electromechanical coupling factor. Consequently, in order to attain a desired distribution of sound pressure of radiation, it is sufficient to provide a desired distribution of electromechanical coupling factor. Since the electromechanical coupling factor depends on intensity of the polarization, control of intensity of the polarization of an piezoelectric transducer causes a desired distribution of sound pressure of radiation, or a desired weighting in amplitude of ultrasounds radiated from the piezoelectric transducer, to be available.

If it is desired to attain a distribution of intensity of the polarization as shown in FIG. 13A, it is sufficient to conduct the polarization up to a saturation state (saturation polarization) for a center of the piezoelectric transducer with respect to the minor axis direction, but it is necessary to conduct an unsaturation polarization for the edge portions thereof.

With respect to the polarization for a center of the piezoelectric transducer with respect to the minor axis direction, that is, the saturation polarization, it is possible to attain the saturation polarization by means of setting the polarization electric field, polarization temperature and/or polarization time as the aforementioned polarization conditions to be sufficiently large, thereby attaining a stabilized constant electromechanical coupling factor, since the polarization is saturated. However, regarding the polarization for the edge portions of the piezoelectric transducer with respect to the minor axis direction, that is, the unsaturation polarization, even though the polarization conditions are exactly controlled, it is difficult to attain a predetermined electromechanical coupling factor because of the peculiar polarization conditions.

FIG. 15 is a graphical representation showing the relations between the polarization condition and the electromechanical coupling factor by way of example.

The graph shown in FIG. 15 represents the relations between the polarization condition and the electromechanical coupling factor in a case where there are prepared a number of piezoelectric transducers, the polarization electric field E is fixed as E=350 V/mm, and the polarization is conducted while varying the polarization temperature and the polarization time.

As seen from FIG. 15, even though the polarization is implemented in the completely same condition, it happens that the electromechanical coupling factor of the piezoelectric transducer after polarization involves the amount of scatter not less than 10%. On the contrary, in order to implement a desired distribution of sound pressure as the aforementioned distribution of sound pressure, it is necessary to suppress the amount of scatter approximately less than 7%.

To suppress the amount of scatter, there is proposed a method (Japanese patent Laid Open Gazette No. 237351/1987) in which the polarization operation is implemented while the polarization state of the piezoelectric transducer is monitored. As disclosed in the above-noted Japanese patent Laid Open Gazette No. 237351/1987, it is possible to identify the polarization state of the piezoelectric transducer by means of measuring frequency characteristics of an electric impedance of the resonance neighborhood of the piezoelectric transducer, alternatively measuring amplitude characteristics of ultrasonic acoustic signals generated by the piezoelectric transducer. To say from the view point that the measurement is conveniently carried out, it is noted that the former, that is, the scheme of measuring frequency characteristics of an electric impedance is more practical.

If this scheme can be utilized well, the amount of scatter in the electromechanical coupling factor ought to be significantly decreased in accordance with such a way that the polarization operation is advanced while the polarization state is monitored, and the polarization operation is terminated when the piezoelectric transducer reaches in intensity of the polarization (electromechanical coupling factor) a predetermined value.

Generally, however, the piezoelectric transducer used in fabrication of the probe is provided with a relatively larger capacitance of the order of tens nF. This involves such a problem that it is difficult to exactly measure frequency characteristics of an electric impedance of the resonance neighborhood of the piezoelectric transducer. The reason why such frequency characteristics can not be measured is that the relatively larger capacitance of the order of tens nF causes a resonance in cooperation with a small inductor component (tens nF) existing on a cable used in measurement of an electric impedance, which cable is connected to the piezoelectric transducer, and thus the electric impedance can not be exactly measured. Even in case of the fabrication of one in which very small pieces of piezoelectric transducer are arranged, such as an array type of probe in which a number of piezoelectric transducers 1 are arranged, as shown in FIG. 9, the probe is temporarily assembled, usually, as mentioned in connection with the explanation of FIG. 13, in a state of piezoelectric transducer having a board-like configuration, and thereafter segmented into very small pieces. Hence, also in this case, when the polarization is carried out, there is given a state of board-like shaped piezoelectric transducer and thus the piezoelectric transducer is provided with a relatively larger capacitance. Accordingly, the similar inconvenience will occur.

As another problem, in case of the implementation of a piezoelectric transducer such that a plurality of stripe configuration of electrodes are arranged on the piezoelectric transducer as shown in FIG. 14, and the respective electrodes are supplied with mutually different polarization conditions (e.g. polarization electric field) so as to practice the above-mentioned amplitude weighting, when the polarization state under some stripe electrode is observed, as shown in FIG. 16, there is such a problem that the portions under other stripe electrodes serve as mechanical loads, and thus it is difficult to exactly measure the polarization state under the portion of interest.

SUMMARY OF THE INVENTION

In view of the foregoing, it is therefore an object of the present invention to provide a method of fabricating an ultrasonic probe provided with a piezoelectric transducer which is small in the amount of scatter in electromechanical coupling factor or in polarization state when the polarization is carried out.

To achieve the above-mentioned object, according to the present invention, there is provided a method of fabricating an ultrasonic probe having piezoelectric transducers undergone a polarization processing, which comprises the steps of: preparing a first piezoelectric transducer for fabrication of said ultrasonic probe and a second piezoelectric transducer for observation of polarization states; and conducting simultaneously polarization processings for both said first and second piezoelectric transducers while observing polarization states of said second piezoelectric transducer.

It is preferable that both said first and second piezoelectric transducers are taken out from a single material of piezoelectric transducer.

Further, it is preferable that in said polarization processing step both said first and second piezoelectric transducers are simultaneously processed for polarization in the same condition.

Furthermore, it is preferable that prior to said polarization processing step, recessions are provided on said second piezoelectric transducer, each extending up to midway in its thickness.

Said polarization processing step is terminated at the time when said second piezoelectric transducer reaches a predetermined polarization state. The polarization state of said second piezoelectric transducer is observed through measurement of electric impedance or electric admittance of said second piezoelectric transducer.

Still further, according to the present invention, there is provided a method of fabricating an ultrasonic probe having piezoelectric transducers undergone a polarization processing, which comprises the steps of: preparing a first piezoelectric transducer for fabrication of said ultrasonic probe and a second piezoelectric transducer for observation of polarization states; conducting polarization processings for both said first and second piezoelectric transducers; and conducting simultaneously depolarization processings for both said first and second piezoelectric transducers while observing polarization states of said second piezoelectric transducer.

It is noted in connection with the present invention as noted above that the aforementioned phrase "while observing polarization states of said second piezoelectric transducer" does not always imply that the polarization states are always continuously observed during the polarization processing or depolarization processing. Such expression may of course imply that the polarization states are always continuously observed, but also may imply that the observation is conducted at regular intervals or at irregular intervals. Further it is noted that in a case where the observation is conducted at regular intervals, it is not necessarily to have to simultaneously in strict meaning conduct both the polarization processing and the observation of polarization states. While it may be of course to do so, it is acceptable to alternately conduct the polarization processing and the observation of polarization states on a switching basis.

According to the present invention, the first piezoelectric transducer for fabrication of an ultrasonic probe and the second piezoelectric transducer for observation of polarization states are cut away from a single material of piezoelectric transducer, and both the first and second piezoelectric transducers are polarized on the same condition while observing the polarization states through the second piezoelectric transducer. It will be possible to indirectly know the polarization states of the first piezoelectric transducer for fabrication of an ultrasonic probe, when observing the polarization states of the second piezoelectric transducer which is cut away from the same material that the first piezoelectric transducer is cut away and has been polarized in the same condition as the first piezoelectric transducer. This feature permits the area of the piezoelectric transducer for observation of polarization states to be selected in such an extent that no effect of the inductance component of the cable is induced, thereby preventing unfavorable resonance at the time of the measurement. Further, in a case where a plurality of stripe-like shaped electrodes are arranged on an piezoelectric transducer so as to practice weighting the amplitude weighting, the implementation of a plurality of second piezoelectric transducers for observation of polarization states each corresponding to the associated electrode makes it possible to exactly measure the polarization states under the respective electrodes independent of the mechanical load.

The above matters have been described assuming that an piezoelectric transducer is increased in polarization intensity up to a predetermined polarization state. It is noted, however, that the present invention is also applicable to such a technique that an piezoelectric transducer is temporarily subjected to the polarization processing (for example, polarizing up to the saturation condition), and thereafter the piezoelectric transducer is subjected to the depolarization processing to deteriorate the polarization intensity (for example, by means of applying the polarization electric field in such a fashion that the polarization intensity is deteriorated). The above discussed technique is disclosed, for example, in Japanese patent Laid Open Gazette No. 237351/1987.

As described above, according to the present invention, from a single material of unpolarized piezoelectric transducer, cut away are a piezoelectric transducer for fabrication of a probe and a piezoelectric transducer for observation of polarization states. Both the piezoelectric transducer for fabrication of a probe and the piezoelectric transducer for observation of polarization states are simultaneously subjected to the polarization processing (or depolarization processing) while observing polarization states of the piezoelectric transducer for observation of polarization states. This feature makes it possible to fabricate an piezoelectric transducer which is polarized in unsaturated state with greater accuracy, thereby fabricating an ultrasonic probe capable of effecting the amplitude weighting with greater accuracy.

DESCRIPTION OF THE PREFERRED EMBODIMENTS

Hereinafter, there will be described embodiments of the present invention.

Figure 1A:
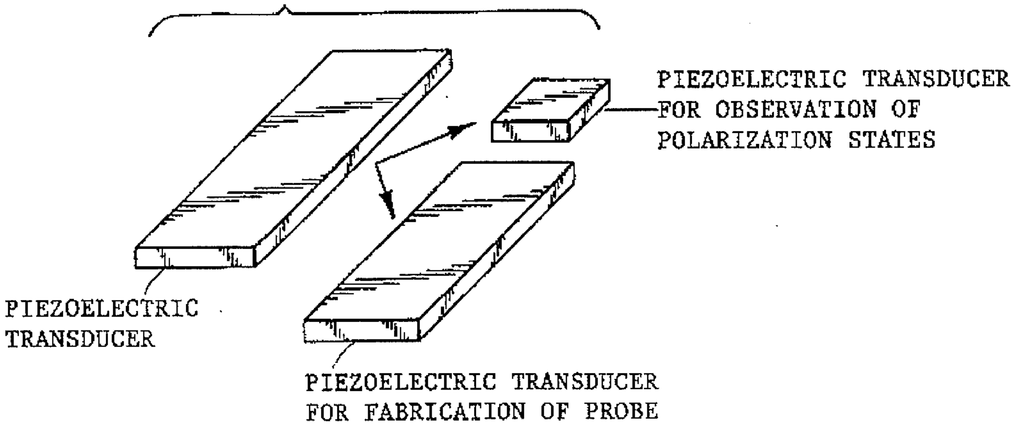
FIGS. 1A and 1B are typical illustrations showing the first embodiment of the present invention.
Figure 1B:
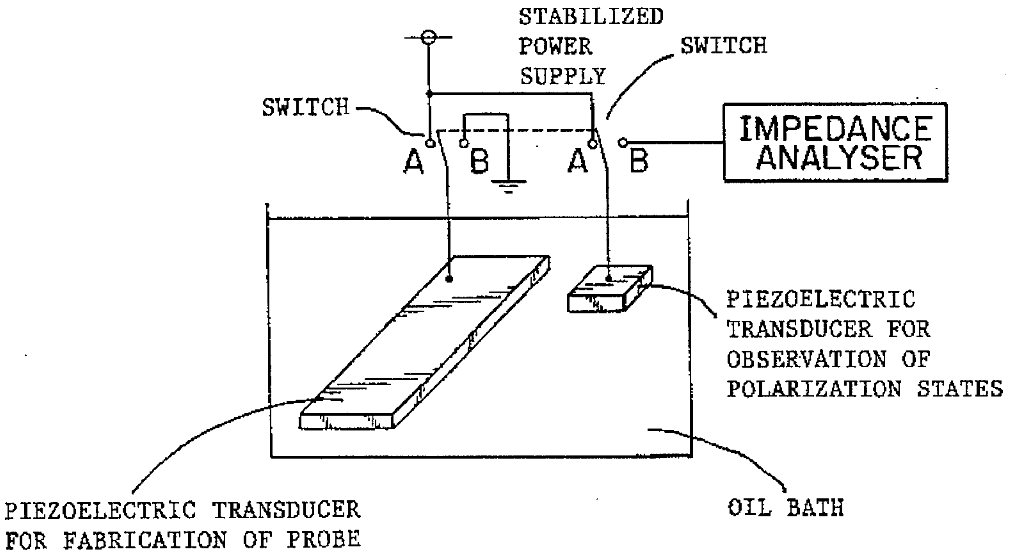

FIGS. 1A and 1B are typical illustrations showing the first embodiment of the present invention.

First, as shown in FIG. 1A, from a single material of unpolarized piezoelectric transducer, cut away are a piezoelectric transducer for fabrication of a probe and a piezoelectric transducer for observation of polarization states. At that time, the piezoelectric transducer for observation of polarization states is cut away with such a size that its capacitance is of less than several nF. As shown in FIG. 1B, both the piezoelectric transducers are soaked into an oil bath to be kept at a specified polarization temperature, and switches are changed over to the contact A side so as to apply a specified polarization electric field through a stabilized power supply to both the piezoelectric transducers. The polarization temperature and the polarization electric field are selected in their values which are sufficient to attain a target electromechanical coupling factor $k_{to}$. After the lapse of a predetermined time since the electric field is applied, the switches are changed over to the contact B side (shut out application of the electric field from the stabilized power supply), so that frequency characteristics of admittance (or impedance) of the piezoelectric transducer for observation of polarization states are observed by the use of an impedance analyzer. From the observed admittance frequency characteristics, resonance frequency $f_r$ and antiresonance frequency $f_a$ of the piezoelectric transducer are determined, and then the electromechanical coupling factor $k_t$ is calculated in accordance with the following formula (2) which is derived from the aforementioned expression (1).

$$k_t = \frac{1}{\sqrt{0.405\frac{f_r}{f_a - f_r} + 0.81}} \tag{2}$$

If the calculated electromechanical coupling factor $k_t$ is less than the target electromechanical coupling factor $k_{to}$, the switches are changed over to the contact A side (disconnect the impedance analyzer) to apply again the polarization electric field to the piezoelectric transducers. The operation for application of the polarization electric field and the operation for measurement of the admittance (measurement of the electromechanical coupling factor) are repeatedly conducted through the switching operation of the switches until the electromechanical coupling factor $k_t$ reaches the target value $k_{to}$. Thus, it is possible to produce the piezoelectric transducer which has been controlled in polarization state with greater accuracy.

Figure 2:
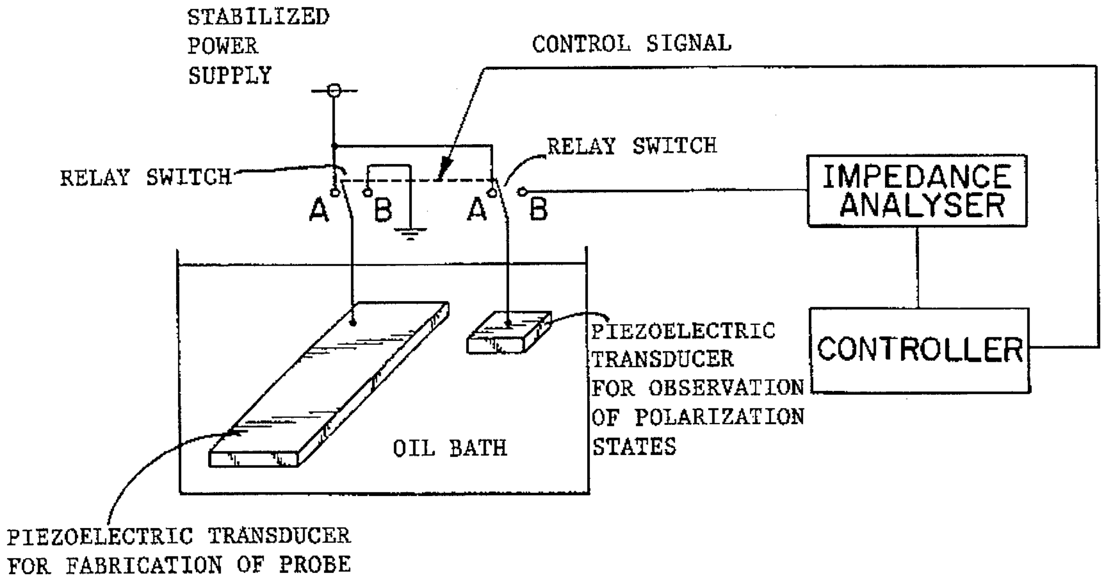
FIG. 2 is a typical illustration showing a modification of the first embodiment of the present invention.

FIG. 2 is a typical illustration showing a modification of the first embodiment of the present invention by way of example.

The modified equipment is provided with an additional controller such as a personal computer, and further relay switches instead of the switches shown in FIGS. 1A–1B which relay switches are adapted to change over the contacts in accordance with a control signal transmitted from the controller. The controller transmits to the relay switches the control signal to instruct the relay switches to change over the contacts to the contacts B every a predetermined time, so that the relay switches are changed over to the contacts B to observe through the impedance analyzer the admittance frequency characteristics of the piezoelectric transducer for observation of polarization states at the switched time point. The observed admittance frequency characteristics are transferred to the controller. In the controller, from the observed admittance frequency characteristics, resonance frequency $f_r$ and antiresonance frequency $f_a$ of the piezoelectric transducer are determined, and then the electromechanical coupling factor $k_t$ is calculated in accordance with the aforementioned formula (2). If the calculated electromechanical coupling factor $k_t$ is less than the target electromechanical coupling factor $k_{to}$, the relay switches are changed over to the contacts A to apply again the polarization electric field to the piezoelectric transducers. The operation for application of the polarization electric field and the operation for the admittance measurement (measurement of the electromechanical coupling factor) are repeatedly conducted, through the switching operation of the relay switches on such a fashion that the relay switches are changed over at regular intervals to the contact B side, until the electromechanical coupling factor $k_t$ reaches the target value $k_{to}$. When the electromechanical coupling factor $k_t$ reaches the target value $k_{to}$, the controller indicates the fact that the polarization operation is terminated, while the relay switches are kept connected to the contacts B. In this manner, the observation of the polarization state may also be placed in an automation.

Figure 3:
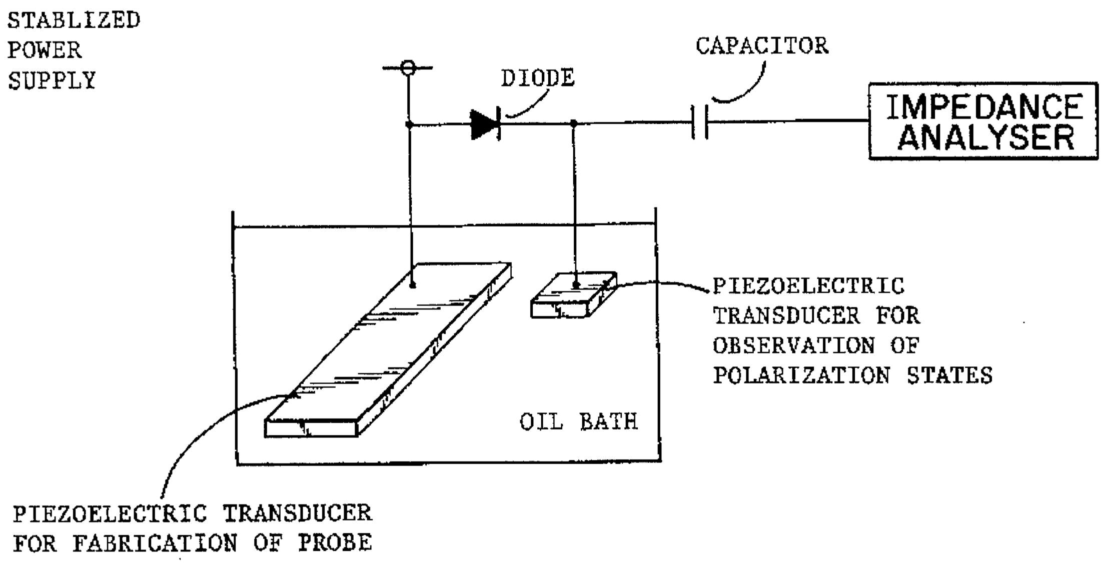
FIG. 3 is a typical illustration showing another modification of the first embodiment of the present invention.

FIG. 3 is a typical illustration showing another modification of the first embodiment of the present invention.

The modified equipment is provided with a diode and a capacitor instead of the switches shown in FIGS. 1A–1B. One end of the diode is connected to the stabilized power supply and the piezoelectric transducer for fabrication of a probe, and the other end is connected to the piezoelectric transducer for observation of polarization states. One end of the capacitor is also connected to the piezoelectric transducer for observation of polarization states, and the other end is connected to the analyzer.

The stabilized power supply serves to apply a DC voltage to the piezoelectric transducer. On the other hand, the impedance analyzer serves to apply an AC voltage to the piezoelectric transducer for observation of polarization states so as to observe the admittance frequency characteristics of the piezoelectric transducer for observation of polarization states. Consequently, the implementation of these diode and capacitor makes it possible to remove the effect of the impedance of the stabilized power supply at the time of the measurement by means of the diode, and to shut out the DC high voltage of the stabilized power supply by means of the capacitor. Thus, it is possible to observe the admittance frequency characteristics of the piezoelectric transducer for observation of polarization states, while the polarization of both the piezoelectric transducers is conducted, without the switching operation of the switches.

Next, the second embodiment of the present invention will be described hereinafter.

Figure 4:
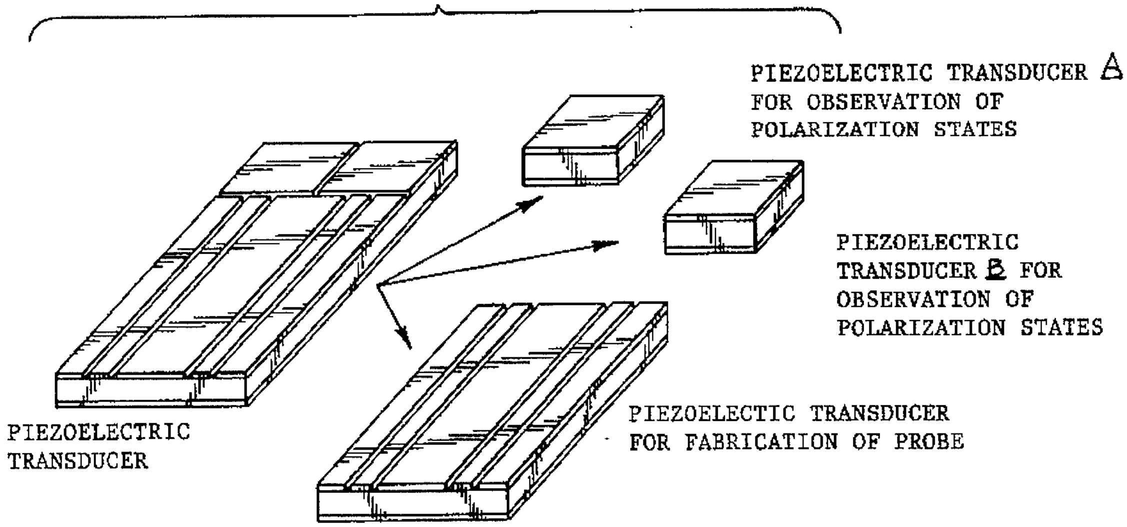
FIG. 4 is a typical illustration showing a process of cutting of piezoelectric transducers according to the second embodiment of the present invention.
Figure 5:
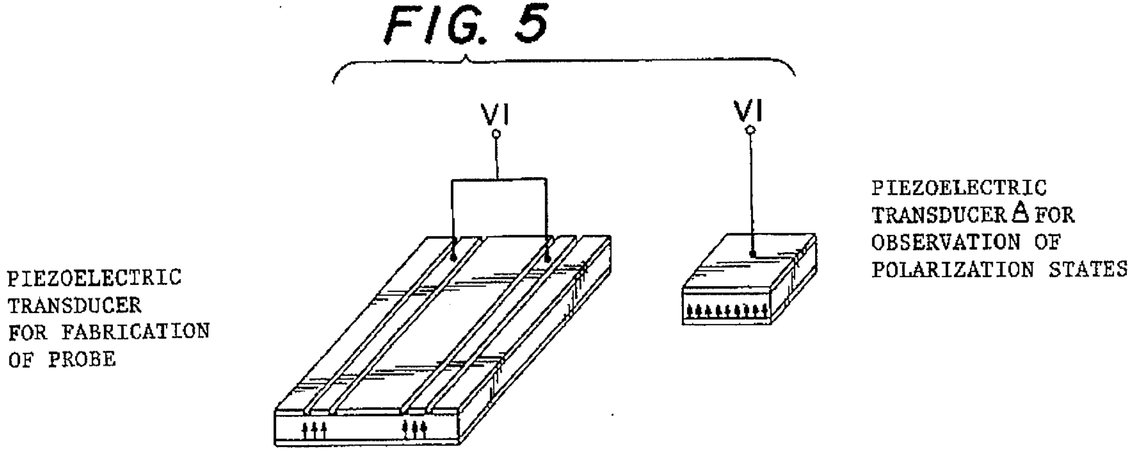
FIG. 5 is a typical illustration showing a process of a polarization disposal according to the second embodiment of the present invention.
Figure 6:
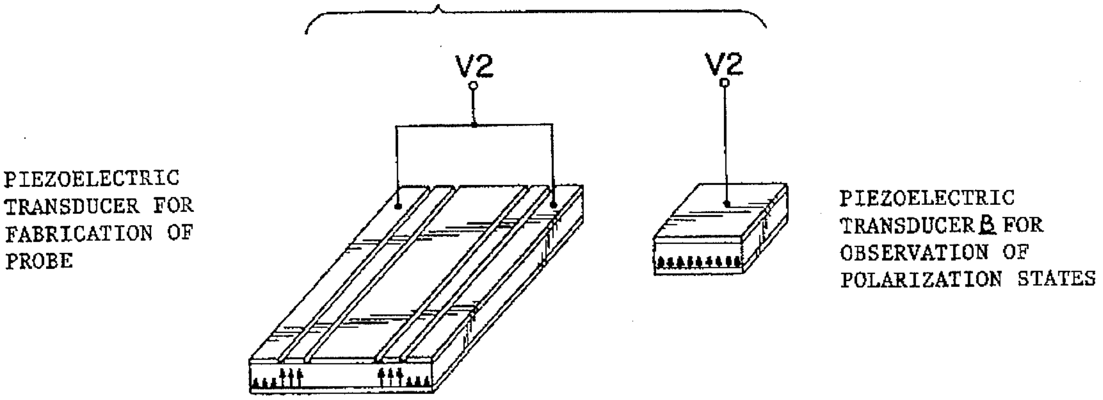
FIG. 6 is a typical illustration showing a process of a polarization disposal according to the second embodiment of the present invention.
Figure 7:
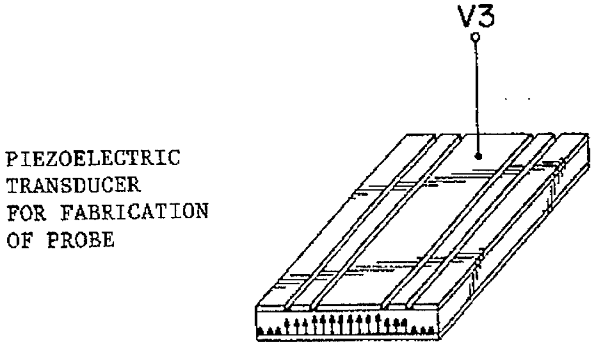
FIG. 7 is a typical illustration showing a process of a polarization disposal according to the second embodiment of the present invention.

FIG. 4 is a typical illustration showing a process of cutting of piezoelectric transducers according to the second embodiment of the present invention. FIGS. 5–7 are each a typical illustration showing a process of a polarization disposal according to the second embodiment of the present invention.

First, as shown in FIG. 4, from a single material of unpolarized piezoelectric transducer, cut away are a piezoelectric transducer for fabrication of a probe, which has a plurality of rows (e.g. 5 rows) of stripe-like shaped electrodes, and piezoelectric transducers for observation of polarization states. At that time, a plurality of pieces (e.g. 2 pieces) of the piezoelectric transducer for observation of polarization states are cut away each with such a size that its capacitance is of less than several nF. Thereafter, as shown in FIG. 5, regarding a pair of stripe electrodes which are located in a symmetrical positional relation with respect to the minor axis direction and a piece of piezoelectric transducer A for observation of polarization states, they are subjected to the polarization processing until the electromechanical coupling factor reaches a predetermined value in accordance with the scheme as mentioned above. And similarly, as shown in FIG. 6, regarding the other pair of stripe electrodes and the other piezoelectric transducer B for observation of polarization states, they are also subjected to the polarization processing until the electromechanical coupling factor reaches a predetermined value. Finally, as shown in FIG. 7, regarding the central stripe electrode, it is subjected to the polarization processing until the saturated polarization state is brought. In this manner, it is possible to reliably fabricate the piezoelectric transducers with greater accuracy to implement the aforementioned amplitude weighting.

Lastly, the third embodiment of the present invention will be described hereinafter.

Figure 8:
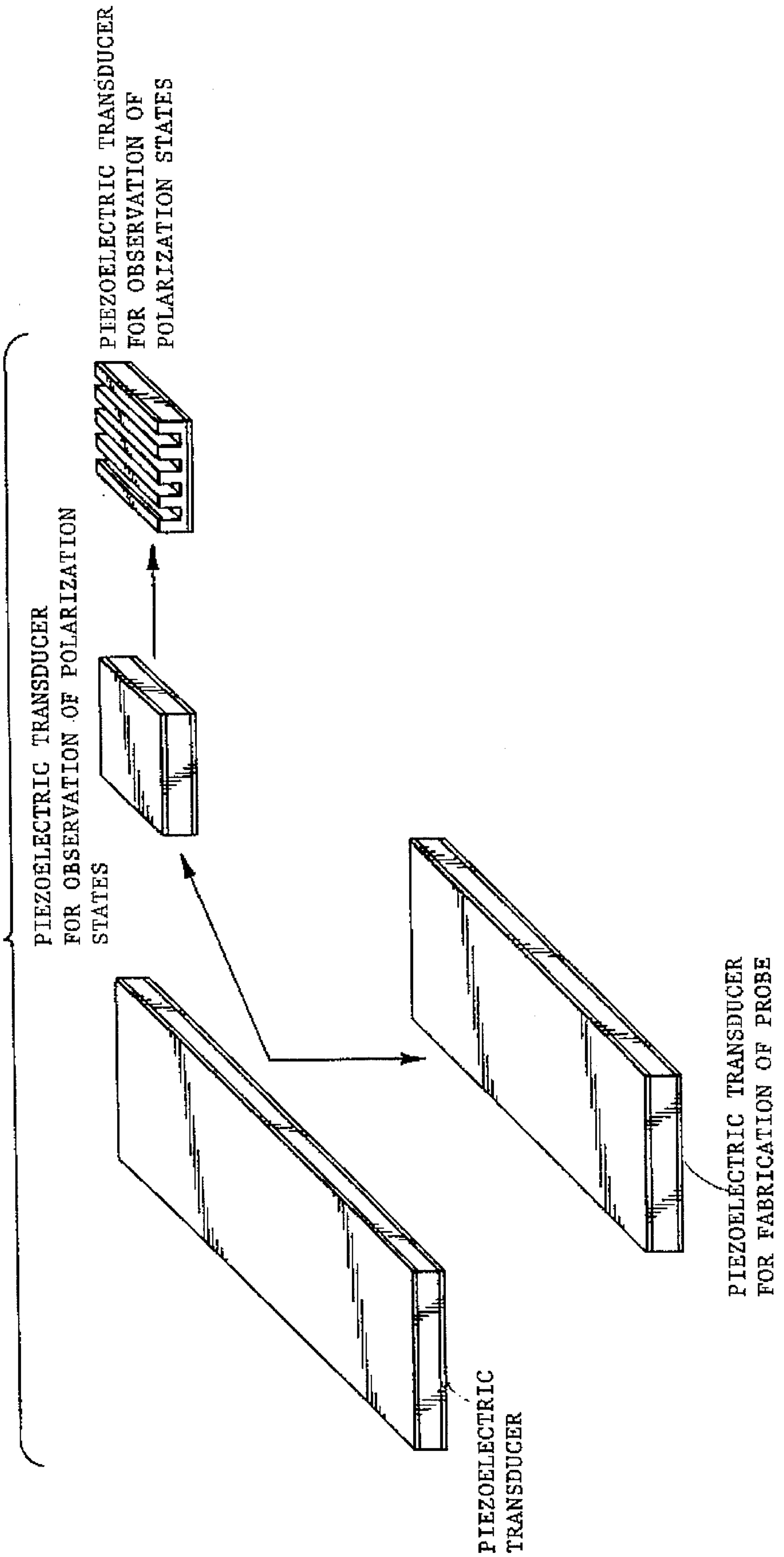
FIG. 8 is a typical illustration showing a process of cutting of piezoelectric transducers according to the third embodiment of the present invention.
Figure 9:
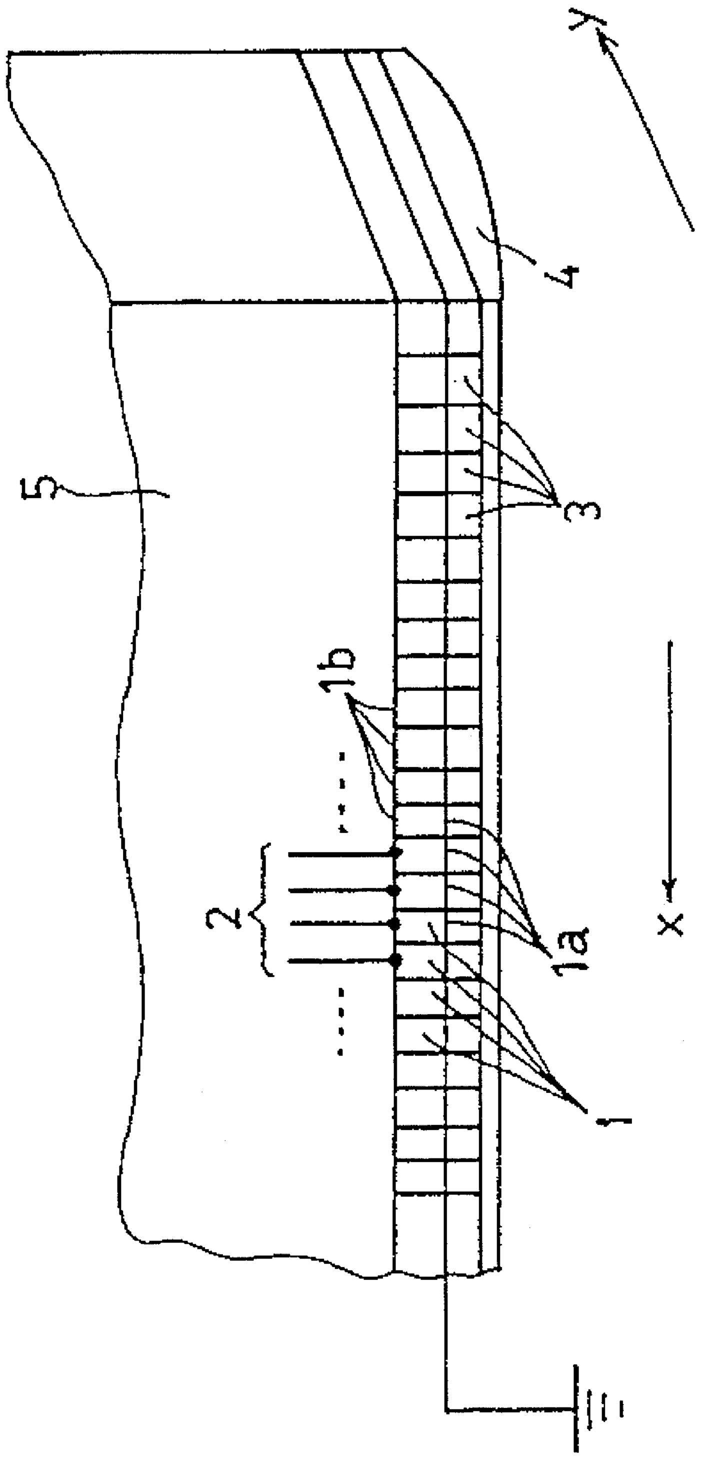
Fig. 9 PRIOR ART
FIG. 9 is a perspective view of an ultrasonic probe by way of example.
Figure 10:
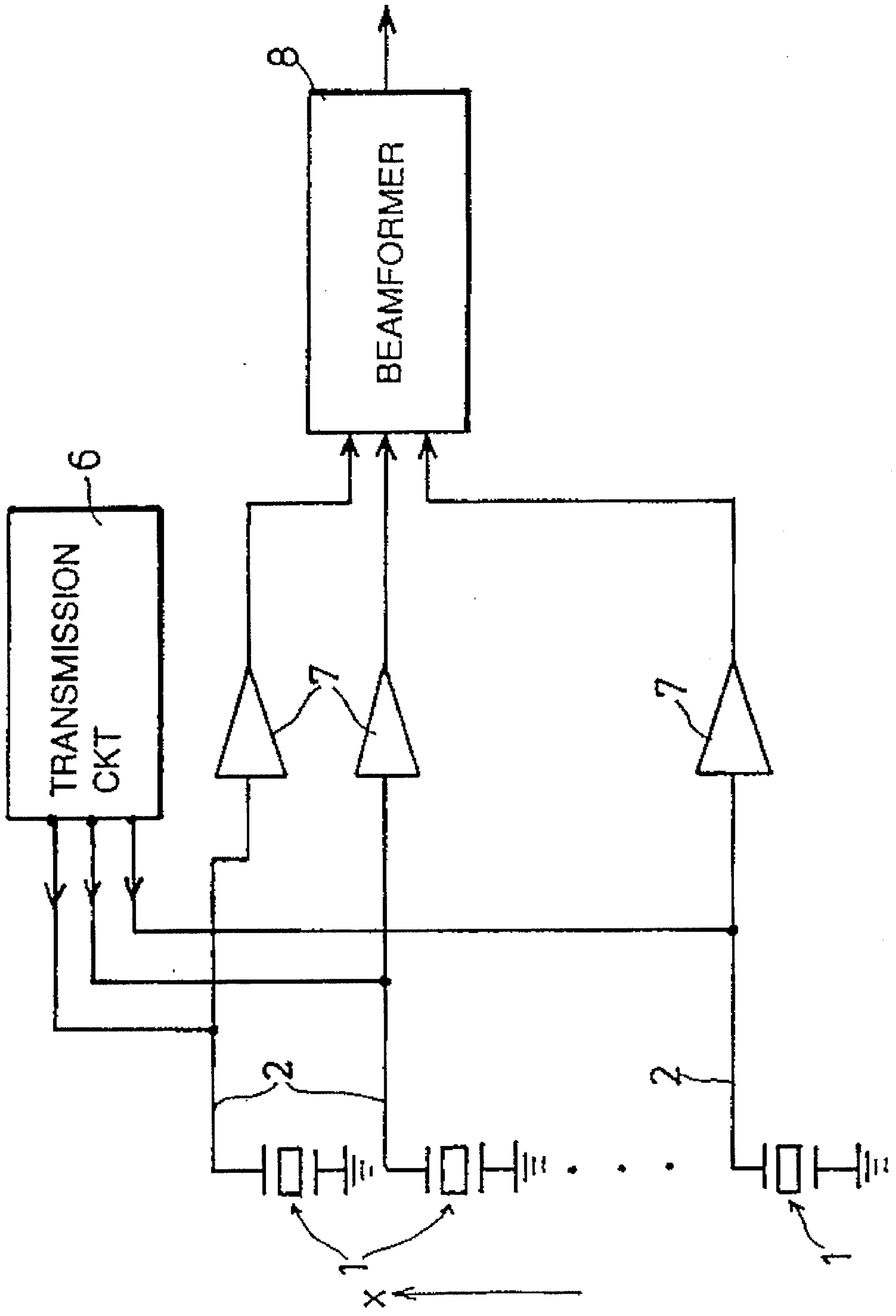
Fig. 10 PRIOR ART
FIG. 10 is a block diagram of circuits to be connected to the ultrasonic probe.
Figure 11A:
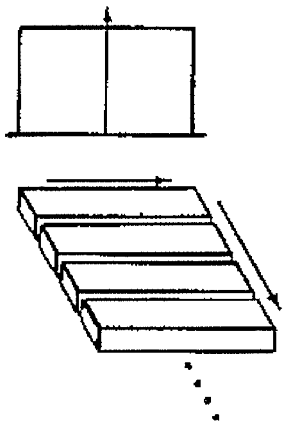
Fig. 11A PRIOR ART
FIG. 11A is a view showing a sound pressure distribution of ultrasounds radiated from an array of piezoelectric transducers.
Figure 11B:
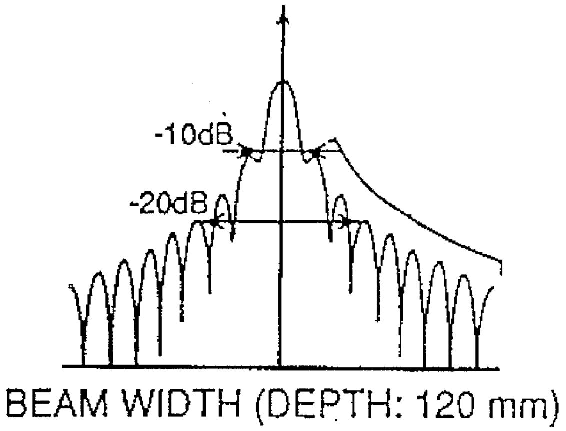
Fig. 11B PRIOR ART
FIG. 11b is a view showing a sound pressure profile of a section of an ultrasonic beam in case of the sound pressure distribution of radiation as shown in FIG. 11A.
Figure 11C:
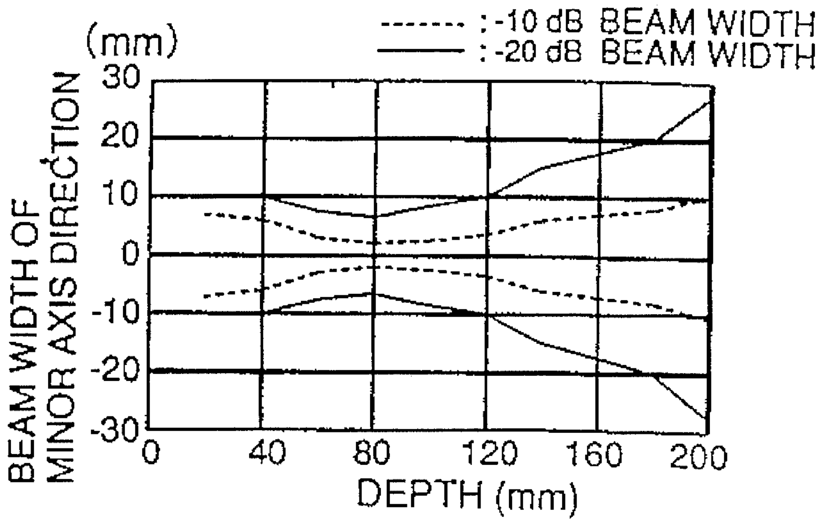
Fig. 11C PRIOR ART
FIG. 11C is a graphical representation showing the relations between the depth within the subject and the beam width of the minor axis direction, in case of the sound pressure distribution of radiation as shown in FIG. 11A.
Figure 12A:
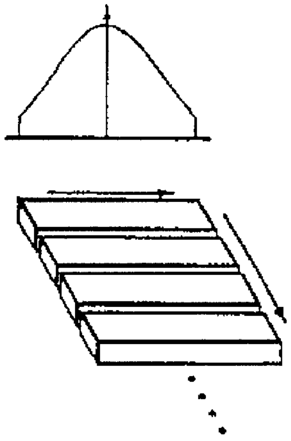
Fig. 12A PRIOR ART
FIGS. 12A–12C are views similar to FIGS. 11A–11C, respectively, except that the sound pressure distribution of radiation is different with respect to the minor axis direction.
Figure 12B:
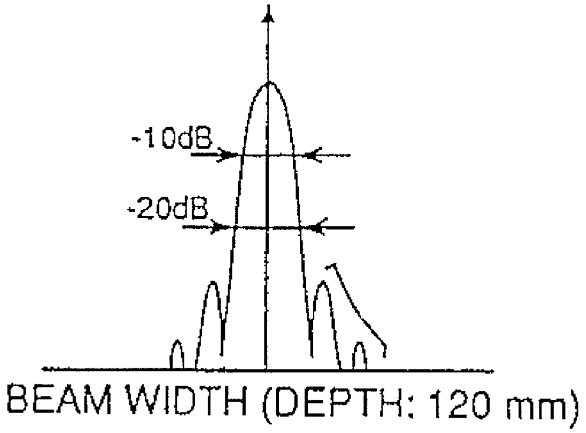
Fig. 12B PRIOR ART
Figure 12C:
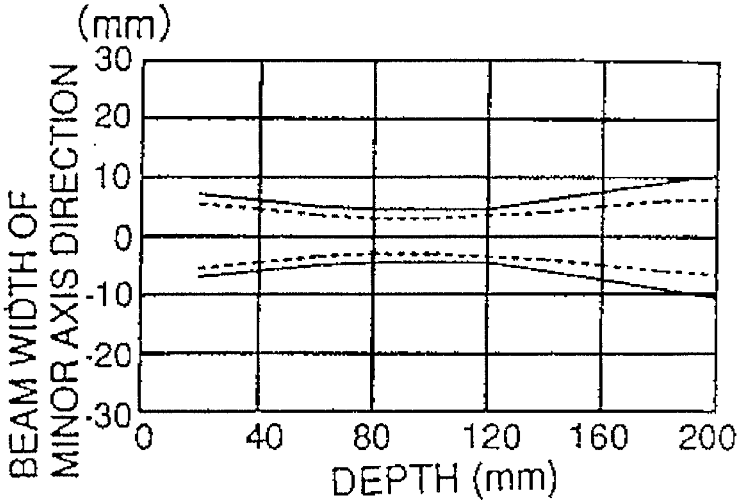
Fig. 12C PRIOR ART
Figures 13A, 13B:
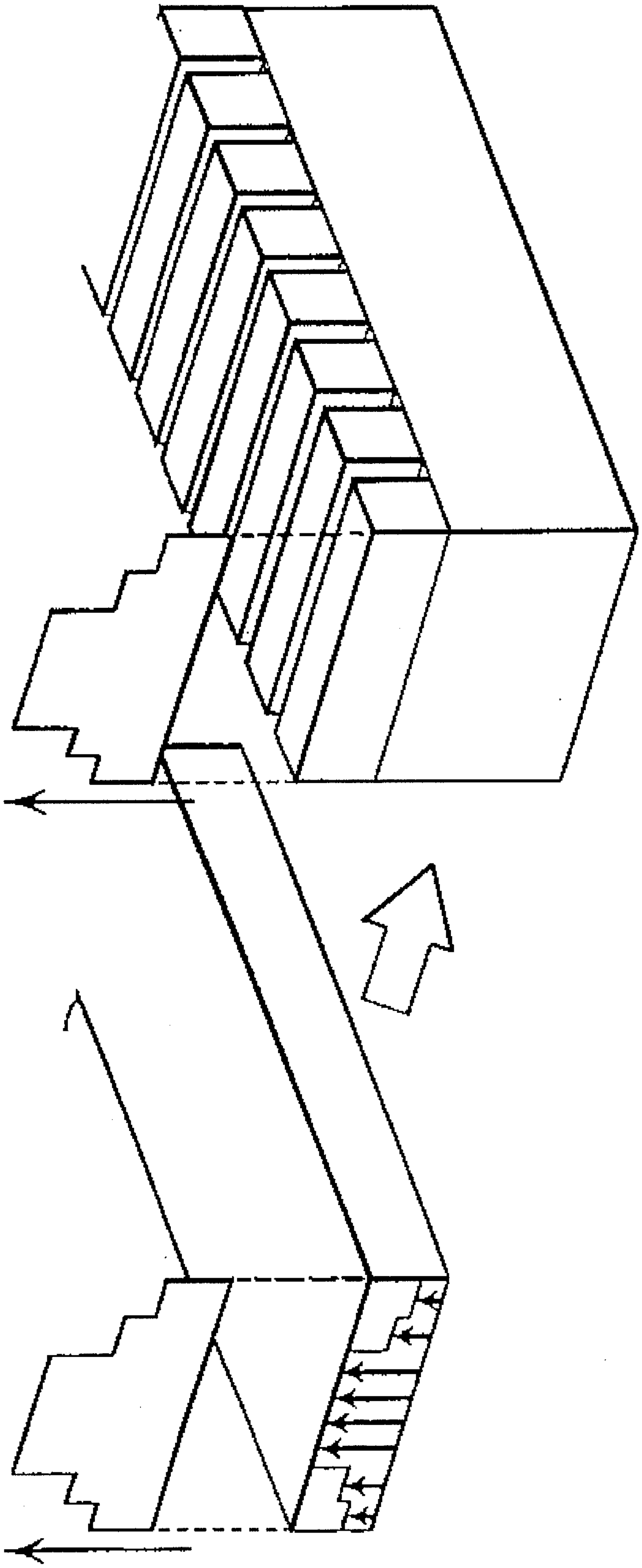
Fig. 13B PRIOR ART
Fig. 13A PRIOR ART
FIGS. 13A and 13B are illustrations showing the relations between a distribution of intensity of polarization of the piezoelectric transducer and a distribution of sound pressure of the radiated ultrasounds.
Figure 14:
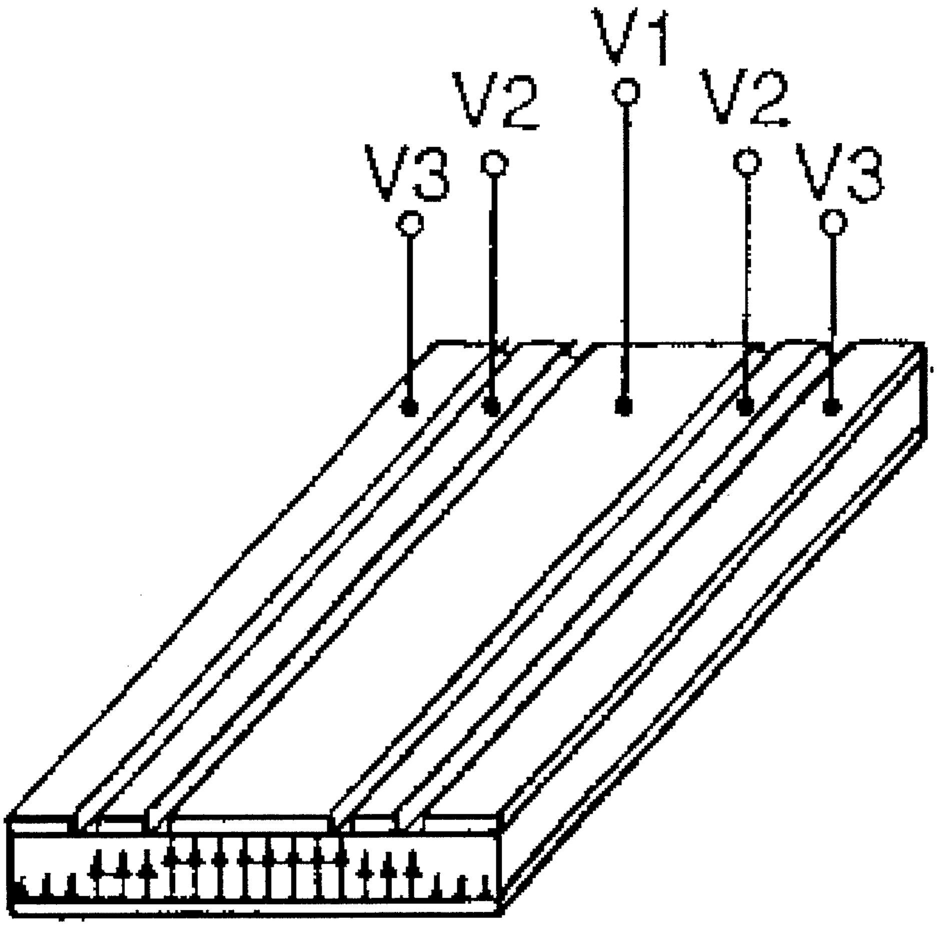
Fig. 14 PRIOR ART
FIG. 14 is a typical illustration showing a technique of polarizing the piezoelectric transducer in such a manner that intensity of the polarization is stepwise given with respect to the minor axis direction.
Figure 15:
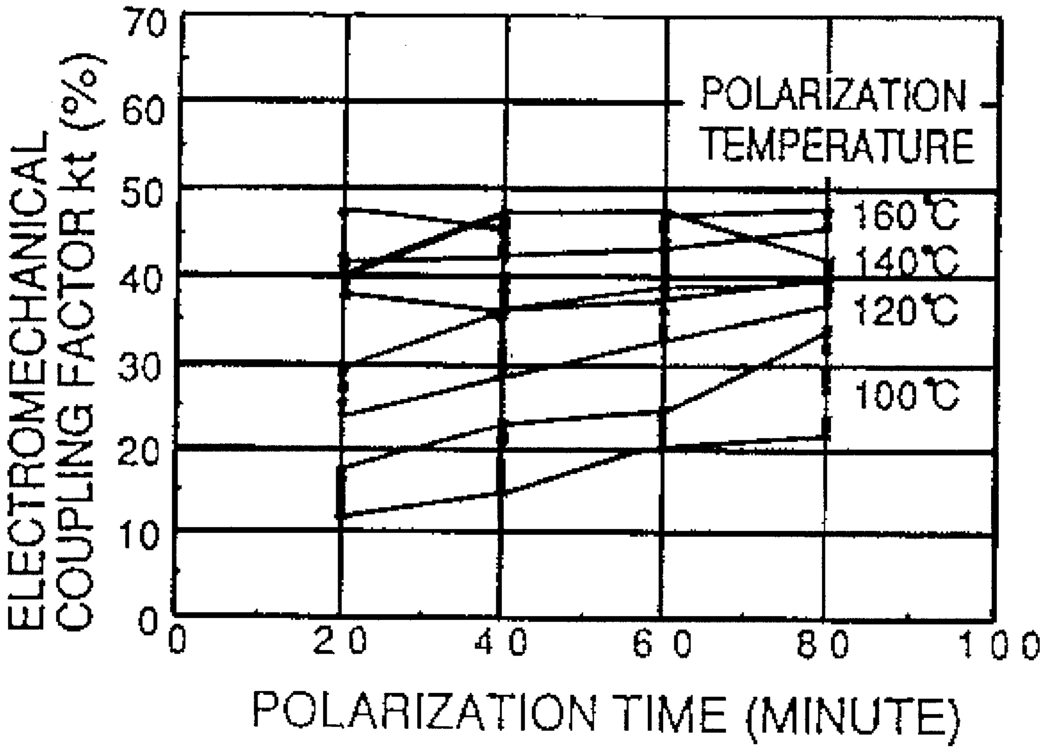
FIG. 15 is a graphical representation showing the relations between the polarization condition and the electromechanical coupling factor.
Figure 16:
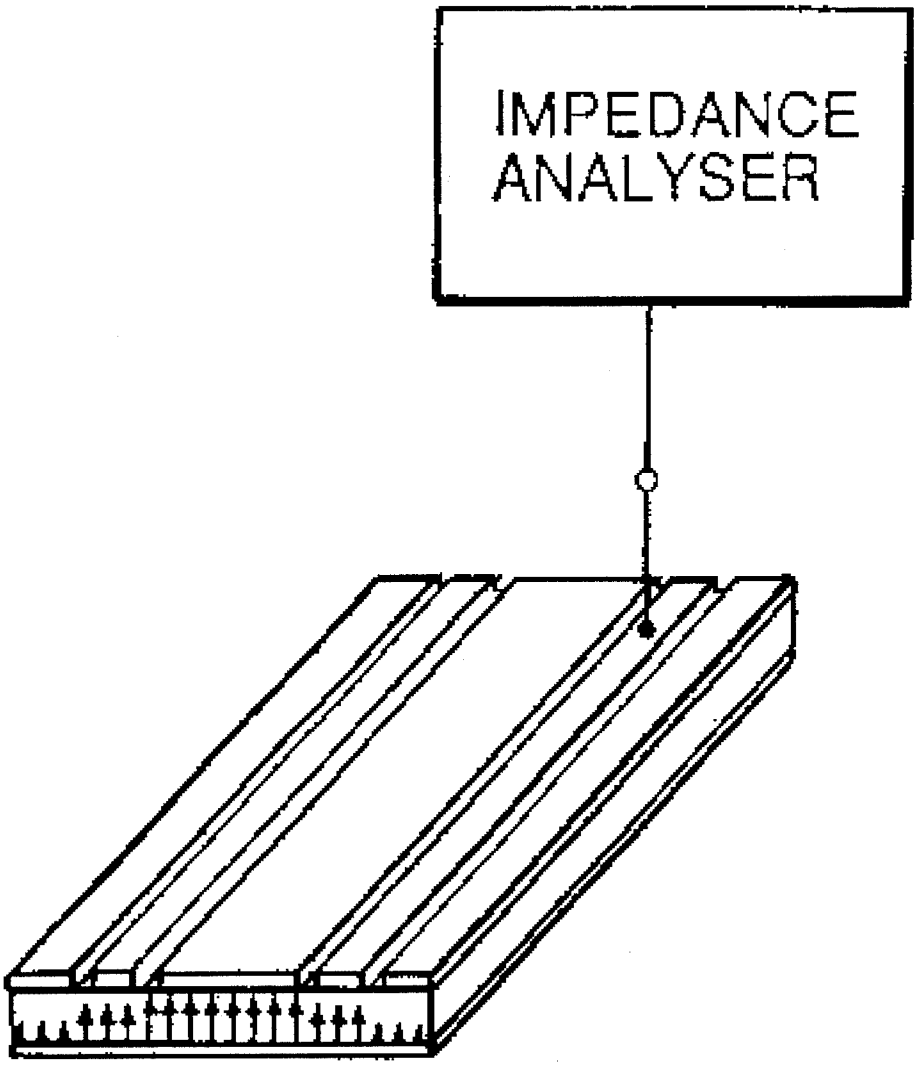
Fig. 16 PRIOR ART
FIG. 16 is a typical illustration useful for explanation of the observation of the polarization state of the piezoelectric transducer having a stripe-like shaped electrode.

FIG. 8 is a typical illustration showing a process of cutting of piezoelectric transducers according to the third embodiment of the present invention.

First, from a single material of unpolarized piezoelectric transducer, cut away are a piezoelectric transducer for fabrication of a probe and a piezoelectric transducer for observation of polarization states. At that time, the piezoelectric transducer for observation of polarization states is cut away with such a size that its capacitance is of less than several nF. The piezoelectric transducer for observation of polarization states is processed to have a plurality of recessions each extending up to midway in its thickness. Thereafter, these piezoelectric transducers are subjected to the polarization processing until the electromechanical coupling factor reaches a predetermined value in accordance with the scheme as mentioned above. When the AC voltage is applied to two main surfaces (upper and lower faces) of a piezoelectric transducer, which main surfaces are each equipped with an electrode, the piezoelectric transducer vibrates with respect to not only the vertical direction, but also the horizontal direction which is parallel to the main surfaces. In a case where in observation of the polarization states, superposition of the resonance of the piezoelectric transducer for observation of polarization states with respect to the horizontal direction on the resonance neighborhood with respect to the vertical direction makes it difficult to conduct the observation, the implementation of the recessions will make it possible to reduce the effect of the resonance with respect to the horizontal direction.

While the present invention has been described with reference to the particular illustrative embodiments, it is not to be restricted by those embodiments but only by the appended claims. It is to be appreciated that those skilled in the art can change or modify the embodiments without departing from the scope and spirit of the present invention.

We claim:

1. A method of fabricating an ultrasonic probe having piezoelectric transducers, comprising the steps of:

preparing a first piezoelectric transducer for fabrication of said ultrasonic probe and a second piezoelectric transducer for observation of polarization states; and conducting simultaneously a polarization processing for both said first and second piezoelectric transducers while observing polarization states of said second piezoelectric transducer.

2. A method of fabricating an ultrasonic probe according to claim 1, wherein both said first and second piezoelectric transducers are made from a single piezoelectric transducer material.

3. A method of fabricating an ultrasonic probe according to claim 1, wherein in said polarization processing step both said first and second piezoelectric transducers are simultaneously processed for polarization in the same condition.

4. A method of fabricating an ultrasonic probe according to claim 1, wherein prior to said polarization processing step, recessions are provided on said second piezoelectric transducer, each extending to one half of its thickness.

5. A method of fabricating an ultrasonic probe according to claim 1, wherein said polarization processing step is terminated when said second piezoelectric transducer reaches a predetermined polarization state.

6. A method of fabricating an ultrasonic probe according to claim 1, wherein the polarization state of said second piezoelectric transducer is observed through a measurement of an electric impedance of an electric admittance of said second piezoelectric transducer.

7. A method of fabricating an ultrasonic probe having piezoelectric transducers, comprising the steps of:

preparing a first piezoelectric transducer for fabrication of said ultrasonic probe and a second piezoelectric transducer for observation of polarization states;

conducting polarization processings for both said first and second piezoelectric transducers; and conducting simultaneously depolarization processings for both said first and second piezoelectric transducers while observing polarization states of said second piezoelectric transducer.

* * * * *